US00PP08743P

United States Patent [19]

Evers

[11] Patent Number: Plant 8,743

[45] Date of Patent: May 24, 1994

[54] FLORIBUNDA ROSE PLANT NAMED 'TANRAVENS'

[75] Inventor: Hans Evers, Uetersen, Fed. Rep. of Germany

[73] Assignee: Bear Creek Gardens, Inc., Medford, Oreg.

[21] Appl. No.: 52,579

[22] Filed: Apr. 22, 1993

[51] Int. Cl.[5] ..... A01H 5/00

[52] U.S. Cl. ..... Plt./28

[58] Field of Search ..... Plt. 28

*Primary Examiner*—Howard J. Locker

*Attorney, Agent, or Firm*—Klarquist Sparkman Campbell Leigh & Whinston

[57] ABSTRACT

A floribunda rose having heavily appendaged sepals; an abundance of small thorns on all branches; a vigorous, upright habit of growth; bright, dark green, glossy and healthy foliage; and bright red flowers borne in large clusters.

1 Drawing Sheet

The present invention relates to a new and distinct variety of rose plant of the floribunda class which was originated by me by crossing the variety TANweieke, U.S. Plant Pat. No. 4,844, with an unnamed seedling.

The primary objective of this breeding was to produce a new rose variety having low, dwarf growth; rich flowering; red color, and good resistance against disease. The objective was substantially achieved along with other desirable improvements as evidenced by the following unique combination of characteristics which are outstanding in the new variety and which distinguish it from its parents, as well as from all other varieties of which I am aware:

1. Very bright red flowers borne in large clusters;
2. Very glossy, dark green, disease-resistant foliage;
3. Vigorous, upright, well-branched growth habit;
4. Abundance of small thorns on all branches; and
5. Presence of heavily appendaged sepals.

Asexual reproduction of this new variety by budding, as performed at Wasco, Calif., and Uetersen, Germany, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—TANweieke, U.S. Plant Pat. No. 4,844.

*Pollen parent.*—An unnamed seedling.

Classification:

*Botanical.*—*Rosa hybrida.*

*Commercial.*—Floribunda.

FLOWER

Observations made from specimens grown in a garden environment in Somis, Calif, from April through November, 1992.

Blooming habit.—Recurrent.

Bud:

*Size.*—1 inch when the petals start to unfurl.

*Form.*—Short, pointed ovoid.

*Color.*—When sepals first divide, bud color is Red Group 43A. When half blown, the upper and lower sides of the petals are Red Group 43A.

*Sepals.*—Color: Green Group 138C, occasionally with a reddish overlay. Surface texture: Covered in fine hairs. There are three normally to heavily appendaged sepals. There are two unappendaged sepals with hairy edges.

*Receptacle.*—Color: Green Group 138B. Shape: Funnel. Size: Medium ($\frac{1}{4} \times \frac{1}{4}$ inch). Surface: Smooth.

*Peduncle.*—Length: Medium (3 to $3\frac{1}{2}$ inches). Surface: Glandular. Color: Medium green and bronzy. Strength: Stiff, erect.

Bloom:

*Size.*—Medium. Average open size is 3 to $3\frac{1}{2}$ inches.

*Borne.*—Singly, several together, in clusters. If in clusters: Rounded.

*Stems.*—Short (8–12 inches), strong.

*Form.*—When first open: High centered. Permanence: Flattens, outer petals curl back.

*Petalage.*—Number of petals under normal conditions: 25.

*Color.*—The upper and reverse sides of the petals are Red Group 43A. The base of each petal has a light yellow half moon ($\frac{1}{4} \times \frac{1}{4}$ inch) at the point of attachment. The major color on the upper side is Red Group 43A.

*Variegations.*—Occasional white streak on the guard petals.

*Discoloration.*—No change in the general tonality at the end of the first day or at the end of the third day.

*Fragrance.*—Slight.

Petals:

*Texture.*—Thick.

*Shape.*—Round.

*Form.*—Tips slightly recurved.

*Arrangement.*—Imbricated, with few petaloids in the center.

*Persistence.*—Drop off cleanly.

*Lastingness.*—On the plant: Fair (5 days). As a cut flower: Fair (6 days).

Reproductive parts:

*Anthers.*—Size: Medium. Quantity: Many. Color: Yellow. Arrangement: Regular around styles.

*Filaments.*—Color: yellow.

*Pollen.*—Color: Gold yellow.

*Styles.*—Color: Red.

*Stigmas.*—Color: Greenish white.

Form: Bush.

Growth: Very vigorous, upright branching.

Foliage: Number of leaflets on normal mid-stem leaves: 5 or 7.

*Size.*—Large (7×4 inches).

*Quantity.*—Abundant.

*Color.*—New foliage: Dark green with reddish color on leaf underside. Old foliage: Dark green, glossy (Green Group 139A).

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth.

*Stipules.*—Medium, bearded.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Hooked downward.

*Color when young.*—Red.

Small Prickles:

*Quantity.*—On main stalks: Many. On laterals: Many.

*Color.*—Brown.

I claim:

1. A new and distinct variety of rose plant of the floribunda class, substantially as herein shown and described, characterized particularly as to novelty by the unique combination of the presence of heavily appendaged sepals; an abundance of small thorns on all branches; a vigorous, upright habit of growth; bright, dark green, glossy and healthy foliage; and bright red flowers borne in large clusters.

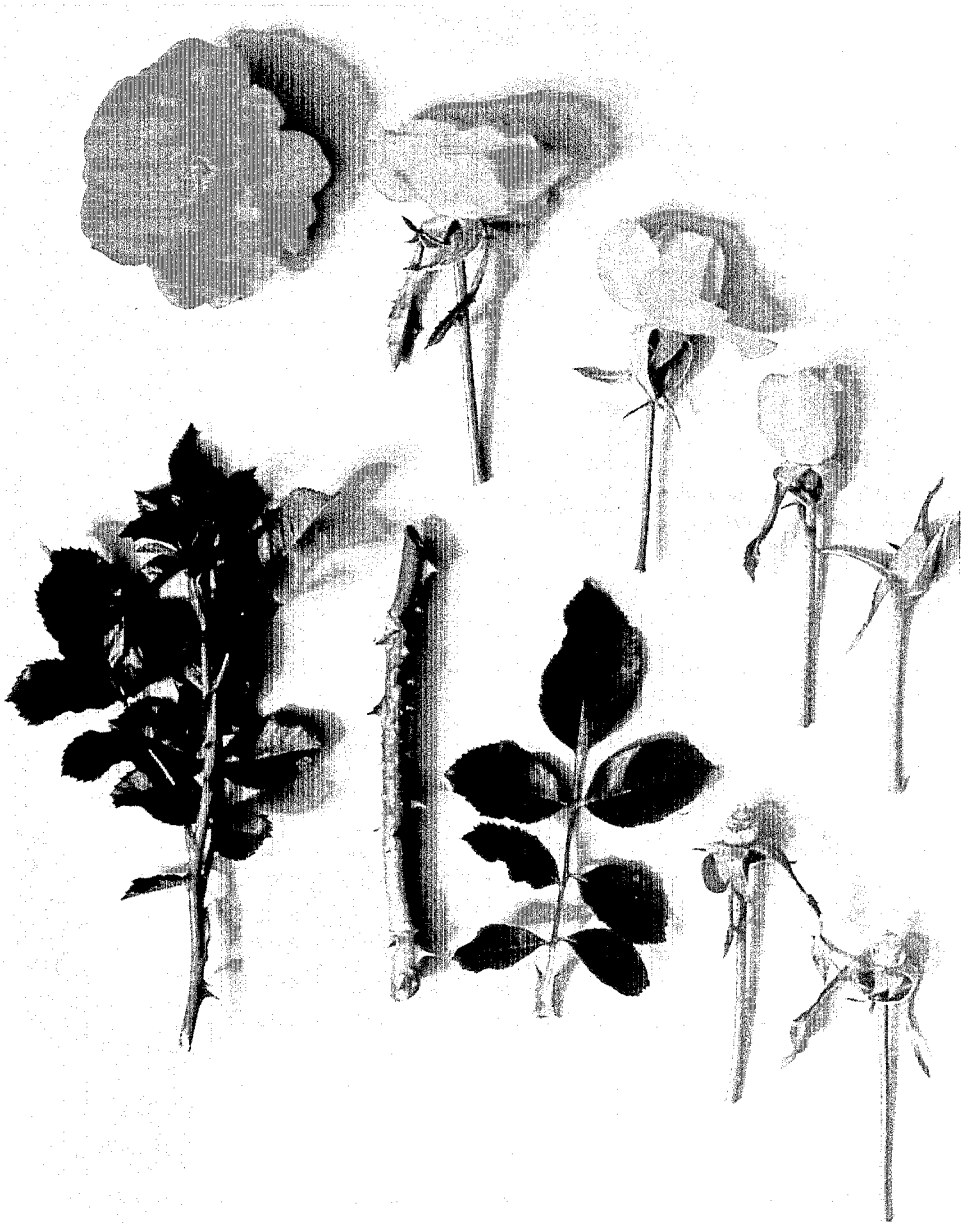

* * * * *